(12) United States Patent
Downing

(10) Patent No.: US 8,211,370 B2
(45) Date of Patent: Jul. 3, 2012

(54) POLYMER SYNTHESIZER

(76) Inventor: Thomas Downing, Roxboro (CA)

( * ) Notice: Subject to any disclaimer, the term of this patent is extended or adjusted under 35 U.S.C. 154(b) by 89 days.

(21) Appl. No.: 11/952,814

(22) Filed: Dec. 7, 2007

(65) Prior Publication Data

US 2009/0148353 A1 Jun. 11, 2009

(51) Int. Cl.
*B01J 19/00* (2006.01)
(52) U.S. Cl. ......................................................... 422/131
(58) Field of Classification Search .................. 422/131
See application file for complete search history.

(56) References Cited

U.S. PATENT DOCUMENTS

| | | | |
|---|---|---|---|
| 5,053,454 A | 10/1991 | Judd | |
| 5,541,314 A | 7/1996 | McGraw | |
| 5,660,792 A | 8/1997 | Koike | |
| 5,681,534 A * | 10/1997 | Neves | 422/131 |
| 5,837,858 A | 11/1998 | Brennan | |
| 6,132,686 A * | 10/2000 | Gallup et al. | 422/130 |
| 6,395,559 B1 * | 5/2002 | Swenson | 506/27 |
| 6,659,142 B2 | 12/2003 | Downs | |
| 6,663,832 B2 | 12/2003 | Lebl | |
| 6,787,112 B1 * | 9/2004 | Turner et al. | 422/130 |
| 6,800,250 B1 | 10/2004 | Hunicke-Smith | |
| 6,868,875 B2 * | 3/2005 | De Beukeleer et al. | 141/130 |
| 6,932,943 B1 * | 8/2005 | Cracauer et al. | 422/130 |
| 7,025,935 B2 | 4/2006 | Jones | |
| 7,033,761 B2 | 4/2006 | Shafer | |
| 7,055,723 B2 | 6/2006 | Ingenhoven | |
| 2002/0028160 A1 * | 3/2002 | Xiao et al. | 422/100 |
| 2003/0113237 A1 | 6/2003 | Cracauer | |
| 2003/0124526 A1 | 7/2003 | Cracauer | |

FOREIGN PATENT DOCUMENTS

WO WO 99/34931 7/1999

* cited by examiner

*Primary Examiner* — Walter D Griffin
*Assistant Examiner* — Christopher Vandeusen
(74) *Attorney, Agent, or Firm* — Brouillette & Partners; Robert Brouillette; François Cartier

(57) ABSTRACT

The present invention provides a polymer synthesizer having a high efficiency production rate. The synthesis of the polymers, and more particularly of DNA and RNA, is done very quickly. Furthermore, it is possible to synthesize a plurality of polymers in the same batch without significantly increasing the time and the complexity of the process.

15 Claims, 4 Drawing Sheets

POLYMER SYNTHESIZER

CROSS-REFERENCE TO RELATED APPLICATIONS

There is no cross-reference to related applications.

FIELD OF THE INVENTION

The present invention generally relates to polymer synthesis. More particularly, the present invention is an improved apparatus which is highly efficient.

BACKGROUND OF THE INVENTION

To meet the increasing demand for nucleic acid synthesis, there has been an increase in the variety of designs, and the volume of production of nucleic acid synthesizers. Unfortunately, the currently available synthesizers are not designed to adequately meet the needs of the industry. In particular, available synthesizers are limited in their ability to efficiently synthesize large numbers of oligonucleotides. While synthesizers have been developed to simultaneously synthesize more than one oligonucleotide at a time, such machines are not efficient at the production of different types of nucleic acids simultaneously (e.g., different lengths of nucleic acids) and are unacceptably prone to performance failures and environmental contamination. Furthermore, available synthesizers are not suitably configured for integration into large-scale automated production facilities.

DNA synthesis is presently performed on automated instruments which are capable of concurrently producing multiple DNA segments. Frequently the apparatus uses reaction columns in which a support material for the reaction is positioned within the columns on top of inert, porous filters, referred to as frits. The support material generally has a starter material bound to the support onto which desired oligonucleotides may be synthesized. The reaction columns are placed within the automated apparatus and chemicals are added to the columns in sequence in appropriate amounts in an automated fashion. In order to address today's large demand for high throughput oligosynthesis, most automated apparatuses have a large footprint and take up a great deal of premium laboratory space.

Most currently known automated synthesizers can produce only a few oligonucleotides at a time, which is limited by the number of reaction columns located within the machines. The number of reaction columns is limited as a practical matter by the increased complexity of the plumbing and valving network, as the number of columns increases. In addition, the system must be airtight to avoid contaminating the chemicals with air or water and to avoid human exposure to the chemicals.

U.S. Pat. No. 5,368,823 issued Nov. 29, 1994, and U.S. Pat. No. 5,541,314 issued Jul. 30, 1996, address the need for producing a large number of oligonucleotides by disclosing a method and apparatus for oligonucleotide synthesis in which the plumbing and valving network is simplified. The patents disclose a system in which there is one supply line and one outlet located in the synthesis chamber for the delivery of reagents into the reaction columns. The outlet can be positioned above the inlet end of each of the columns so that nucleotide reagents, capping reagents, deblocking reagents, wash chemicals, etc. can be provided to each of the reaction columns. All of the reagents are located in a supply system which includes reservoirs and valving to connect the reservoirs with the supply line. A flush/prime column is also located within the chamber so that the supply line can be flushed and primed between each different chemical reagent addition. A vacuum source, located outside of the reaction chamber, is connected to the outlet end of the reaction columns to rapidly draw the chemicals from all columns simultaneously, thus leaving the columns dry and ready to receive the next reagent.

The disclosed apparatus in these two patents provides multiple reaction columns, but the single supply line requires flushing and priming between the addition of each reagent. These steps are time consuming and waste reagents. Moreover, a large footprint is required to accommodate a reaction chamber encompassing the moving supply line and the reaction chambers as well as a vacuum source outside of the reaction chamber. The large footprint is a drawback to space-constrained laboratories.

Another group of patents, U.S. Pat. No. 5,472,672 issued Dec. 5, 1995, U.S. Pat. No. 5,529,756 issued Jun. 25, 1996, and U.S. Pat. No. 5,837,858 issued Nov. 17, 1998, addresses the need for high throughput oligosynthesis by disclosing a polymer synthesis apparatus with many stationary supply lines. The patents disclose an apparatus with a head assembly with many nozzles, with each nozzle coupled to a reagent reservoir. Further, a base assembly has at least one reaction well but can utilize 96-well and other plates. A transport mechanism is coupled to the head assembly and/or base assembly to produce relative movement between the two. The transport mechanism moves horizontally to align a selected reaction well and a selected nozzle to deposit a selected liquid reagent into the reaction well for synthesis of a polymer chain. A sliding seal is positioned between the head assembly and the base assembly to form a common chamber that encloses both the reaction wells and nozzles therein. The seal is constantly being rubbed down by the movement of the metal piece back and forth to move the synthesis block. This wearing down of the seal results in a less efficient seal.

Thus, the art is in need of polymer synthesizers that are efficient, flexible, and are amenable to large-scale production and automation for the synthesis of polymer, and more specifically of DNA.

OBJECTS OF THE INVENTION

It is a first object of the present invention to provide an apparatus to synthesize polymers having high output efficiency.

Another object of the present invention is to provide an apparatus to synthesize polymers which needs less inert gas during the synthesis.

A further object of the present invention is to provide an apparatus to synthesize polymers which is capable of producing a plurality of polymers in the same batch.

Other and further objects and advantages of the present invention will be obvious upon an understanding of the illustrative embodiments about to be described or will be indicated in the appended claims, and various advantages not referred to herein will occur to one skilled in the art upon employment of the invention in practice.

SUMMARY OF THE INVENTION

A polymer synthesizer having an airtight cabinet configured to maintain a positive gas pressure, comprising a lid, synthesis columns having a lower extremity, and connected to a plurality of reagent containers through reagent dispense lines and wherein the reagents are dispensed with tip dispensers into the synthesis columns, comprising a block comprising a plurality of waste columns disposed in groups, each of the waste column being adapted to receive the lower extremity of one of the synthesis column; a plurality of waste channels, wherein each waste column of one of the groups is continuously connected to a single waste channel, and wherein all of the groups are simultaneously connected to their corresponding waste channels; and a plurality of waste channel valves connected to each of the waste channels to selectively drain at least one of the waste channels.

The polymer synthesizer may be used to synthesize polymers with a flow-through process, such as, for example, oligonucleotides, peptide nucleic acids (PNA), polypeptides, nucleic acids, DNA or RNA. The containers may also contain the solutions used in the reactions, such as deblocking agent, washing solution, coupling activator, capping agent, oxidizer or other solutions required for a reaction, which are also designated by the term "reagent" in the present document.

The synthesis columns are sealingly connected into the waste columns of the block to make an airtight fit with sealing means such as, for example, pressure fit, a flat mat or an o-ring. However, any other suitable sealing means may be used for this purpose. The synthesis of a polymer occurs in the synthesis column in a derivatized Controlled Porosity Glass (further referred as CPG), which is a solid support for covalent attachment of biological molecule, or parent molecule, as known in the art. The solid support can be derivatized CPG, polystyrene or any other convenient material having a large surface area and capable of being derivitized (during the process of derivitization, a protected nucleotide or linker is attached to which the growing DNA chain is attached). The CPG is a white powder held between two porous plastic frits. Other solid phase supports may also be held between frits or imbedded in a solid frit. The reagents are dispensed at the top of the synthesis column and left for an appropriate time, and then drained through waste column by overpressure. The sealed box in which all of this occurs is continuously pressurized. When a valve is opened to provide an exit pathway then the reagents on the columns will flow out the exit pathway provided. The next step of the synthesis is then carried out as others reagents are dispensed into the column until the polymer is completed. The reagents are dispensed into the synthesis columns by tip dispensers, which are controlled by valves, connected to the corresponding pressurized reagent containers. The number of tip dispensers installed on an apparatus is variable and adapted to the occurring synthesis. Furthermore, it is possible to synthesize different polymers in the different synthesis columns in the same batch or the same block. To further improve the efficiency of the apparatus, when multiple reagents are dispensed sequentially into the same synthesis columns without drainage, the less reactive reagent may be dispensed first into the corresponding synthesis column to save time and then the other reagents are dispensed. Usually the reagent containers (and order of dispensing) are alphabetically ordered with the name of the reagent but in the present invention, the reagent containers are decreasingly ordered depending of the reagent reactivity increasing again the efficiency of the apparatus. To further improve efficiency and to avoid errors, the synthesis columns may be optically identified and verified by their color when they are color coded, prior to or at the beginning of a synthesis run, as known in prior art.

The airtight cabinet has a lid on the top to place or remove the block and the synthesis columns. The tip dispensers are sealingly fixed in the lid and a translucent window may be installed in the lid. They may be threaded to the lid or inserted in a hole and sealed with sealing means. The lid configuration may be interchangeable to allow a different number or configuration of the tip dispensers.

To displace the block, two linear slides, controlled by a servomotor or step motor, are used in both the y and x axes in a horizontal plane. The block may be adapted to be disposed directly on the slides or on a movable plate connected on the slides and adapted to receive a block. This block is moved so as to place the appropriate synthesis column under one of the dispense tips so that a specific reagent can be dispensed into that synthesis column. An optical device may be used to identify a synthesis column prior to the displacement. A plurality of synthesis column may be filled by a plurality of tip dispensers at the same time with different reagents. The motion of the slides is controlled by a computer which sends the appropriate instructions to the valves and motion controllers of the slides. The computer can be either on-board or outside the apparatus. Several polymer synthesizers can be controlled by one computer.

The block is used to hold the synthesis columns by their lower extremity and to drain the waste, or used reagents, to a waste container. The block is a structure having a two dimensional matrix of vertical holes, or waste columns, that are connected to a waste container through waste channels. The waste channels may drain the waste of a plurality of synthesis columns or only one synthesis column. The evacuation of a plurality of waste columns or a sole waste column is controlled by a valve installed on the waste line that is preferably controlled by a computer. The reagent is allowed to stay in the synthesis column for a defined amount of time and is drained through the synthesis column to waste with overpressure when the waste valve is opened. Because a plurality of waste columns or a sole column may be controlled independently from the others, there is no need to wait for other longer reactions to drain wastes, increasing the efficiency of the apparatus. Each group of columns which is continuously connected to a waste channel functions independently of the other groups or banks. Each group may therefore use an entirely different synthesis cycle. A purge waste port is also provided to drain and/or to prime a dispense lines.

The block may be composed by only one part or by a plurality or parts. For example, the block may be composed by two parts; a spacer block, or top part, and an o-ring block or bottom part. The idea is to fix the sealing means, in this case o-rings, in the waste columns of the bottom part. When the synthesis columns are inserted in the two part block, the pressure tight seal is made by the pressure of the o-ring on the column. This allows for a more effective seal since the columns may have a slightly different size. In addition, the pressure required to insert or remove the columns is much less than in a design with a pressure fit to fix the synthesis column into the waste columns. In this example the sealing means are inserted into the bottom part but they may be inserted at the bottom extremity of the spacer or any other suitable positions.

A support may be used to hold a plurality of synthesis columns. The support allows the columns to be inserted all at once and is then inserted and removed as a unit into the block. Using a dimensionally slightly modified version of this same block, multiwell plates or synthesis plates may also be used in which the wells comprise an opening at their lower extremity and acts as synthesis columns.

The present invention provides also a method to synthesize one or more polymer by simultaneously chemically linking a plurality of monomers to a plurality of parent molecules. The method allow the making at least one type of polymers by chemically linking a plurality of monomers to a parent molecule attached in a synthesis column one at a time in an apparatus comprising an airtight cabinet with a lid, a block having a plurality of waste columns disposed on a horizontal plane having x and y axles, a plurality of synthesis columns connected to waste columns of said block by their lower extremity, and reagents being delivered from a plurality of reagent containers through reagent dispense lines and wherein the reagents are dispensed with tip dispensers into synthesis columns, the waste columns being controlled by waste valves, the method comprises displacing the block along both y axis and x axis to dispense reagents in synthesis columns through tip dispensers with means to displace said block, draining the synthesis columns by the opening of waste valves, repeating the dispensing of reagents and the draining of synthesis columns as needed for a polymer.

The chemical linkage may be, for example, a phosphodiester bond, a phosphorothioate bond, a phosphonate bond, a phosphoramidate bond, an amide bond, an imine bond, a carbamate bond, an azo bond, a sulfone bond, a sulfonide bond, a sulfonamide bond, a sulfide bond, a disulfide bond, an ether bond, an ester bond, a thiourea bond, a urea bond or a carbon-carbon bond.

The polymers synthesized by the present polymer synthesizer may be nucleic acids, DNA, RNA, peptide nucleic acids (PNA), polypeptides or any other product suitable for preparation by solid phase synthesis. The monomer may be a modified nucleotide comprising a minor groove binder.

In a preferred embodiment, the steps to create a molecule by chemical linkage include:
 a. washing the support on which is attached to one or more parent molecules;
 b. dispensing a liquid comprising a deblocking agent to remove the protecting group attached to the parent molecule;
 c. draining the liquid comprising the deblocking agent;
 d. washing the support;
 e. dispensing a liquid comprising a coupling activator;
 f. dispensing a liquid comprising a protected nucleotide;
 g. draining the liquid comprising a protected nucleotide;
 h. dispensing a liquid comprising a capping agent;
 i. draining the liquid comprising the capping agent;
 j. washing the support;
 k. dispensing a liquid comprising an oxidizer;
 l. draining the liquid comprising the oxidizer.

It is to be noted that the previous sequence is for only one monomer added. Any of the operations of this sequence may be repeated when necessary depending of the resulting polymers to be synthesized.

The features of the present invention, which are believed to be novel, are set forth with particularity in the appended claims.

BRIEF DESCRIPTION OF THE DRAWINGS

The above and other objects, features and advantages of the invention will become more readily apparent from the following description, reference being made to the accompanying drawings in which.

DETAILED DESCRIPTION OF THE PREFERRED EMBODIMENT

A novel polymer synthesizer will be described hereinafter. Although the invention is described in terms of specific illustrative embodiment(s), it is to be understood that the embodiment(s) described herein are by way of example only and that the scope of the invention is not intended to be limited thereby.

Figure 1:
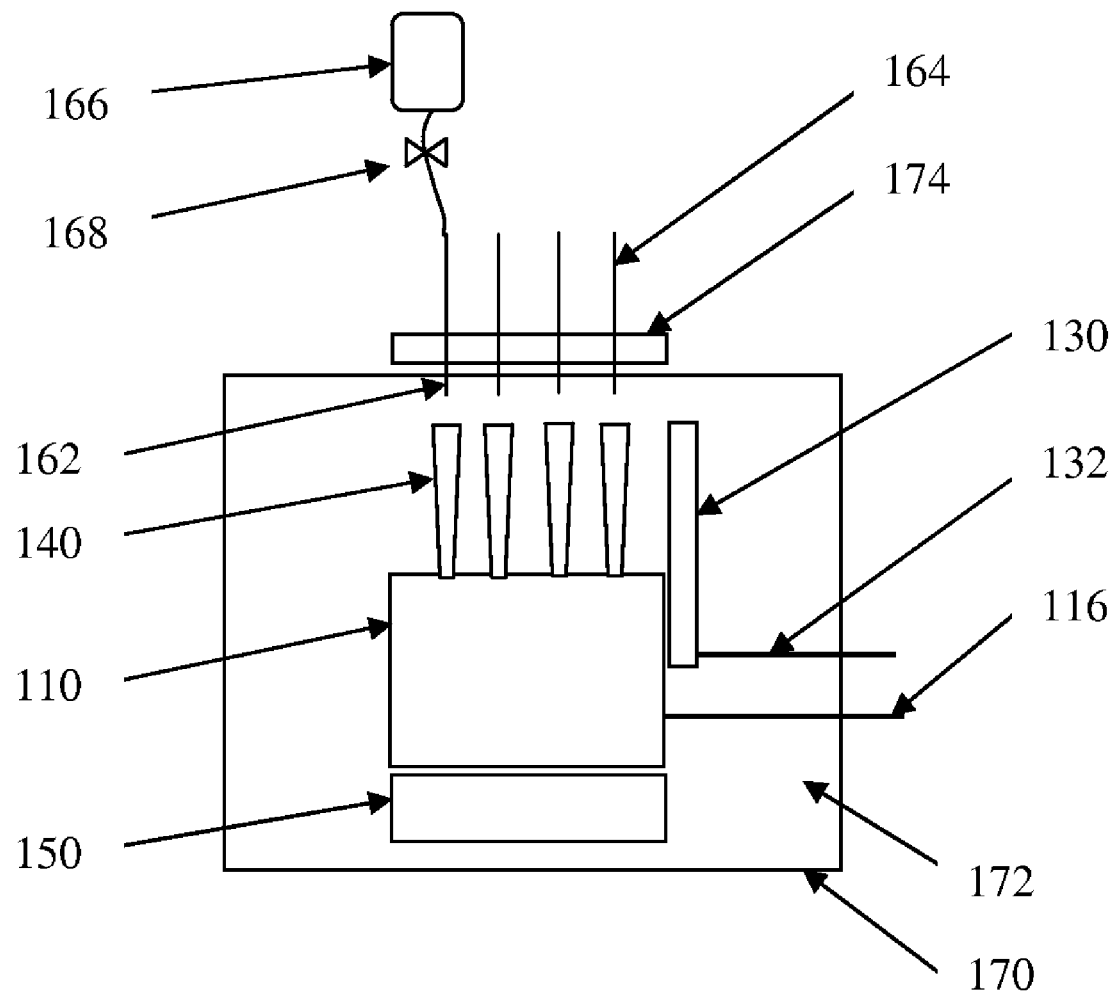
FIG. 1 is a cross-sectional schematic side view showing the polymer synthesizer and its principal components.

The FIG. 1 shows the polymer synthesizer and its principal components. The process occurs in the airtight cabinet 170 which defines an internal chamber 172. The chamber 172 is filled with an inert gas such as argon or nitrogen, for example, to create a positive pressure in the cabinet. There is a hermetic lid 174 on the top of the cabinet 170. There is a window (not shown), which is fixed in the lid 174 holds the tip dispensers 162. These tip dispensers 162 are connected to the reagent dispense lines 164 which are connected to the pressurized reagent containers 166 and the dispensing is controlled by the reagent valves 168 (only one set of reagent container and reagent valve is shown).

The synthesis occurs in the synthesis column 140 which are connected to the block 110. The reagents are carried to the synthesis column 140 through the tip dispensers 162. The block 110 comprises the waste columns (not visible in FIG. 1, 412 in FIGS. 4 and 612 in FIGS. 6a and 6b) and the waste channel 116 that are connected to a waste container (not shown). The block 110 is displaced by the plate 150. A purge waste port 130 is connected to a waste container (not shown) with the outlet 132 or purge waste port channel.

Figure 2:
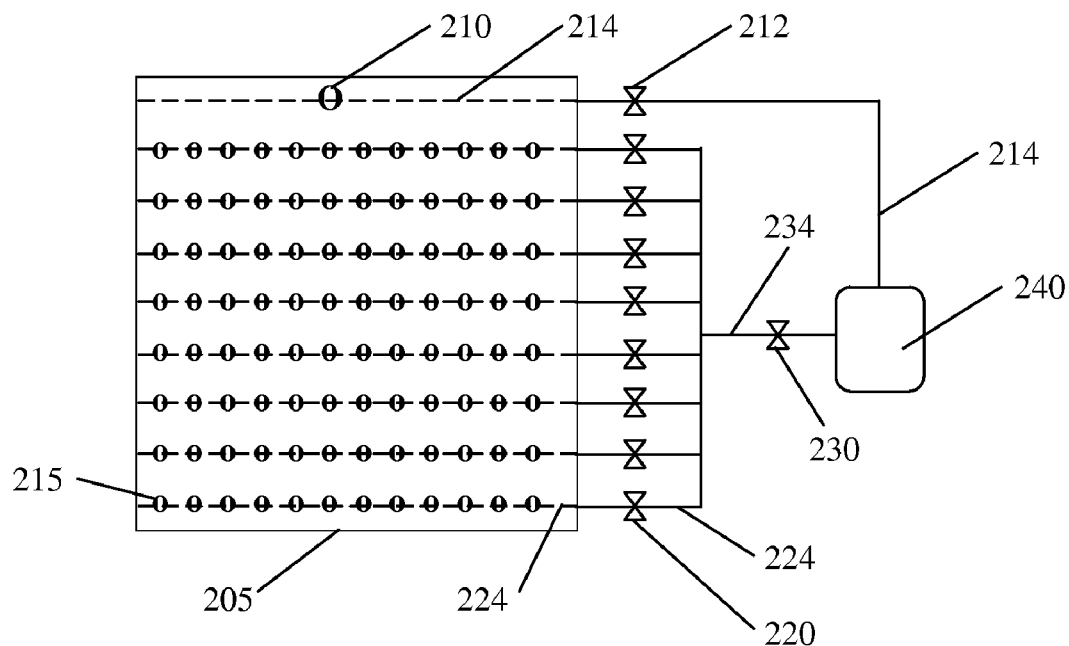
FIG. 2 is a schematic top view showing the waste lines organization.

The wastes are drained with a plurality of lines of waste channels forming the waste system shown in FIG. 2. In a first embodiment, the waste columns are regrouped in the block 205 in a two dimensional matrix for the waste evacuation. As seen in the FIG. 2, the waste channel 224 connects the waste columns 215 of a row, a row corresponding to a group of at least one waste column. The waste channel valve 220 controls the evacuation of the waste channel 224 to the waste container 240. The container valve 230 controls the inlet of the waste container 240. All the channels are connected to the common waste line 234. The purge waste port 210 is connected to the waste container 240 through the purge waste line 214 and is controlled by the purge waste line valve 212.

Figure 3:
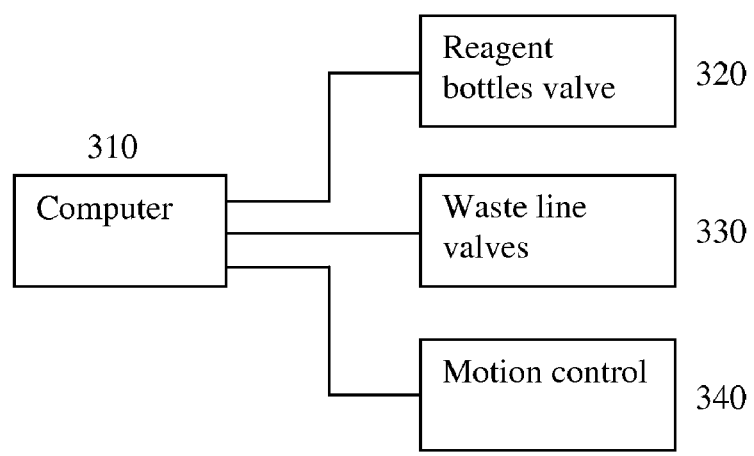
FIG. 3 is a schematic diagram of the control system of the polymer synthesizer.

The polymer synthesizer is controlled by a control system as shown in FIG. 3. The computer 310 controls the reagent container valves 320, the waste valves 330 and the motion control to move the plate 340.

Figure 4:
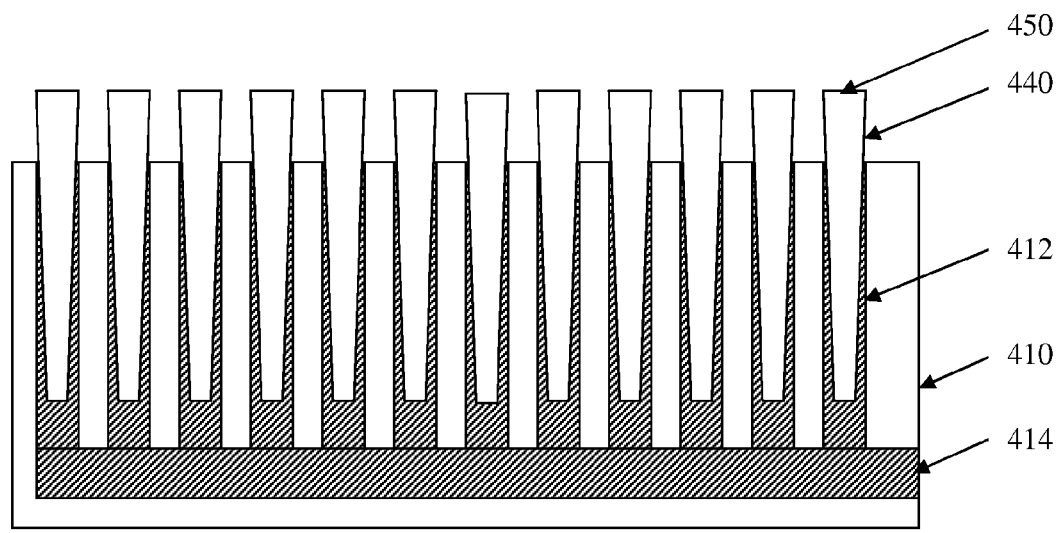
FIG. 4 is a cross-sectional side view showing a first embodiment of the block.

A first embodiment for the block 410 is shown in FIG. 4. The synthesis column 440 receives the reagent product from the tip dispensers (not shown) by the inlet 450. The synthesis column 440 is adapted to hermetically fit with a waste column 412 and the waste are expelled into a waste container (not shown) through the waste channel 414.

Figure 5A:
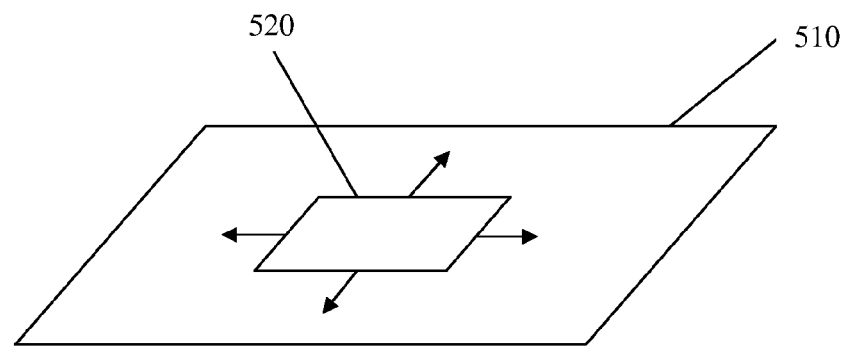
FIGS. 5a and 5b are perspective views showing the motion of the plate and of the block.
Figure 5B:
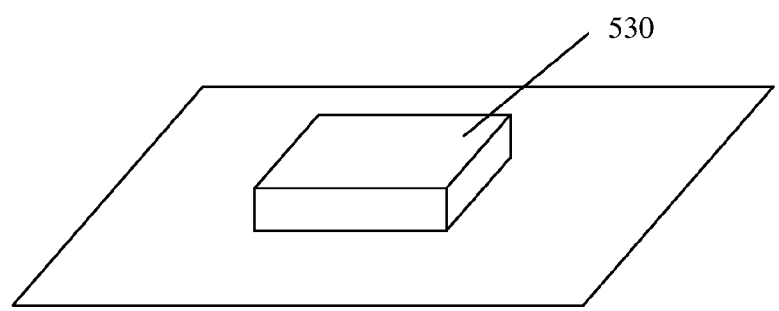

The motion of the plate 520 is shown in FIG. 5a, the surface of the plate 520 is adapted to receive a block. The surface 510 represents the bottom of the airtight cabinet (not shown). A second embodiment is shown in FIG. 5b, where the block itself 530 is displaced without a plate.

Figure 6A:
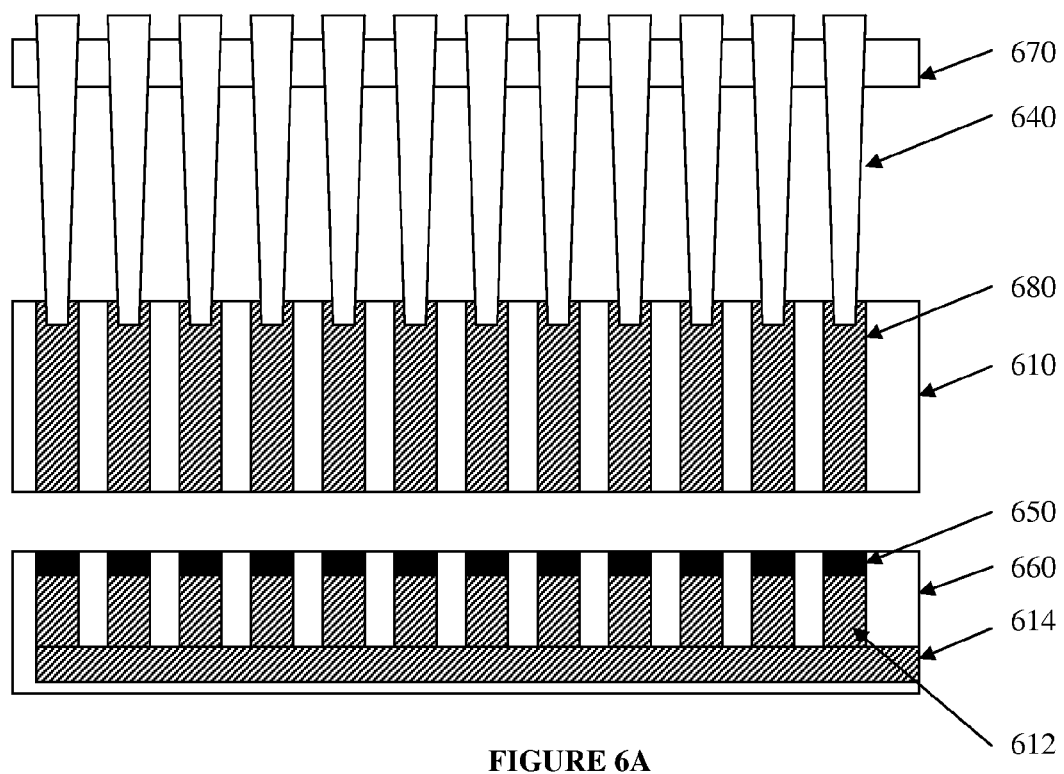
FIGS. 6a and 6b are cross-sectional side views showing a second embodiment of the block, FIG. 6a being an exploded view of the different parts and the FIG. 6b a view as assembled.
Figure 6B:
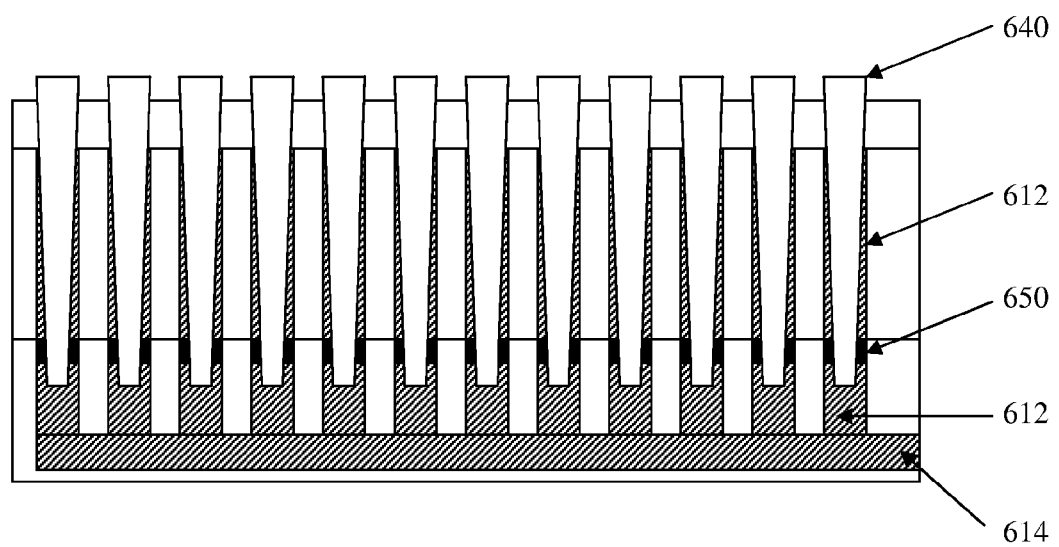

FIGS. 6a and 6b show a second embodiment for the block which is constituted by two part, the spacer block, or top part, 610 and the o-ring block, or bottom part, 660. The synthesis columns 640 are hold by a support 670. The lower parts of the synthesis columns 640 are forced into the o-rings 650 to make an airtight fit. The synthesis columns 640 are inserted in the top part 610 of the block through the openings 680. The wastes are expelled thought the wastes columns 612 and drained into a waste container (not shown) by the waste channel 614. It is to be noted that the block may be constituted by only one part also with the o-rings fixed in the waste columns.

While illustrative and presently preferred embodiment(s) of the invention have been described in detail hereinabove, it is to be understood that the inventive concepts may be otherwise variously embodied and employed and that the appended claims are intended to be construed to include such variations except insofar as limited by the prior art.

The invention claimed is:

1. A polymer synthesizer for synthesizing one or more polymers, said synthesizer comprising an airtight cabinet configured to maintain therein a positive gas pressure, said cabinet comprising a lid and having mounted therein a plurality of tip dispensers, each one of said tip dispensers being connectable to a reagent container via a reagent dispense line and a reagent dispense valve, said synthesizer comprising:
   a. a plurality of synthesis columns, each of said synthesis columns being configured to receive at least one reagent in order to synthesize at least one polymer, each of said synthesis columns comprising an upper extremity and a lower extremity;
   b. a block comprising a plurality of waste columns and a plurality of waste channels, said waste columns being disposed into groups such that for each of said groups, every waste column is simultaneously and continuously fluidly connected to one of said waste channels, each of said waste channels being fluidly connected to a waste valve and each of said waste valves being continuously fluidly connected to a waste system such that every waste columns of one or more of said groups can be simultaneously drained at any given time and independently of other said groups, at least some of said waste columns having sealingly received therein said lower extremity of one of said synthesis columns, said block being displaceable in a substantially horizontal plane along two perpendicular axes wherein said block is displaced along both of the axes independently of the other axis such as to align at least one of said synthesis columns with at least one of said tip dispensers in order for said at least one of said synthesis columns to receive said at least one reagent.

2. The polymer synthesizer of claim 1, further comprising means to displace said block along said two perpendicular axes, said means to displace said block comprising at least a slide that can move along said substantially horizontal plane and on which said block is disposed.

3. The polymer synthesizer of claim 1, further comprising means to displace said block along said two perpendicular axes, said means to displace said block comprising a movable plate connected to a pair of slides that can move along said horizontal plane and on which said block is disposed.

4. The polymer synthesizer of claim 1, further comprising an optical device to identify a synthesis column.

5. The polymer synthesizer of claim 1, wherein said block may be composed by a plurality of parts.

6. The polymer synthesizer of claim 1, wherein said block is composed by a top part and a bottom part.

7. The polymer synthesizer of claim 1, wherein said synthesis columns are sealingly connected to said waste columns with sealing means.

8. The polymer synthesizer of claim 7, wherein said sealing means is a pressure fit.

9. The polymer synthesizer of claim 7, wherein said sealing means is an o-ring.

10. The polymer synthesizer of claim 1, further comprising a purge waste port.

11. The polymer synthesizer of claim 10, wherein said purge waste port is drained through a waste channel.

12. The polymer synthesizer of claim 1, wherein said waste system comprises a common waste line continuously fluidly connected to each of said waste valves in order for said common waste line to drain one or more of said waste channels.

13. The polymer synthesizer of claim 12, wherein said common waste line is fluidly connected to a common waste line valve.

14. The polymer synthesizer of claim 1, wherein said airtight cabinet has a positive pressure.

15. The polymer synthesizer of claim 1, wherein said airtight cabinet is filled with an inert gas.

* * * * *